(12) United States Patent
Shutko et al.

(10) Patent No.: US 8,762,175 B1
(45) Date of Patent: Jun. 24, 2014

(54) METHODS AND SYSTEMS FOR PROMOTING MOBILE AWARENESS

(75) Inventors: Alan T. Shutko, St. Louis, MO (US); Mark G. Bini, O'Fallon, MO (US)

(73) Assignee: Express Scripts, Inc., St. Louis, MO (US)

(*) Notice: Subject to any disclaimer, the term of this patent is extended or adjusted under 35 U.S.C. 154(b) by 0 days.

(21) Appl. No.: 13/316,329

(22) Filed: Dec. 9, 2011

(51) Int. Cl.
G06Q 50/00 (2012.01)
G06Q 10/00 (2012.01)

(52) U.S. Cl.
USPC .................................... 705/3; 705/2

(58) Field of Classification Search
USPC .................................... 705/2, 3, 4
See application file for complete search history.

(56) References Cited

U.S. PATENT DOCUMENTS

| | | | |
|---|---|---|---|
| 2006/0031097 A1* | 2/2006 | Lipscher et al. | 705/2 |
| 2007/0192142 A1* | 8/2007 | Nicholson et al. | 705/3 |
| 2007/0250341 A1* | 10/2007 | Howe et al. | 705/2 |
| 2008/0091468 A1* | 4/2008 | Heidenreich et al. | 705/3 |
| 2008/0248815 A1* | 10/2008 | Busch | 455/456.5 |
| 2009/0119129 A1* | 5/2009 | Nadas et al. | 705/3 |
| 2010/0030580 A1* | 2/2010 | Salwan | 705/3 |
| 2010/0287001 A1* | 11/2010 | Pearce et al. | 705/2 |
| 2013/0006663 A1* | 1/2013 | Bertha et al. | 705/3 |

FOREIGN PATENT DOCUMENTS

WO WO 2006055515 A1 * 5/2006

OTHER PUBLICATIONS

Duru, Kenrik, "Mail-Order Pharmacy Use and Adherence to Diabetes-Related Medications," Jan. 2010, Am J Manag Care, 16(1): 33-40.*

* cited by examiner

Primary Examiner — Elaine Gort
Assistant Examiner — John Go
(74) Attorney, Agent, or Firm — Husch Blackwell LLP

(57) ABSTRACT

Methods and systems for promoting mobile awareness are described. In an embodiment, a location associated with a member of a drug benefit plan is accessed. A drug benefit plan action is determined based on the location associated with the member. The drug benefit plan action is an action at least partially at the direction of a pharmacy benefit manager that administers the drug benefit plan. A drug benefit notification is generated based on the drug benefit plan action. The pharmacy notification benefit is associated with the drug benefit plan. Additional methods and systems are disclosed.

13 Claims, 12 Drawing Sheets

METHODS AND SYSTEMS FOR PROMOTING MOBILE AWARENESS

FIELD

The field relates to mobile electronic devices, and more particularly to promoting mobile awareness through the use of mobile electronic devices.

BACKGROUND

Pharmacy benefit managers (PBMs) offer different provider network or pharmacy networks as part of a benefit plan design that includes a prescription drug benefit. These pharmacy or provider networks include the locations at which a member of a benefit plan may have a prescription for a drug filled. These locations may include retail locations, mail order locations, or both retail and mail order locations. The amount of money a member may pay at retail for the drug may depend upon on the pharmacy provider network associated with the retail location and/or the reimbursement rate paid by the PBM to the retail location.

DETAILED DESCRIPTION

Example methods and systems for promoting mobile awareness are described. In the following description, for purposes of explanation, numerous specific details are set forth in order to provide a thorough understanding of example embodiments. It will be evident, however, to one of ordinary skill in the art that embodiments of the invention may be practiced without these specific details.

Generally, a client engages a pharmacy benefit manager (PBM) to offer a drug benefit program to members. Examples of clients include governmental organizations (e.g., Federal government agencies, the Department of Defense, the Centers for Medicare and Medicaid Services and state government agencies), middle market companies, large national employers, health insurance companies that have carved out the drug benefit, and the like. The PBM may be a stand-alone PBM, or may be part of a larger organization that offers other benefits or services. The methods and systems may generally be used to guide a person who is a member of the drug benefit program offered by the client to pharmacies associated with a pharmacy network or pharmacy network association. Pharmacy networks and pharmacy network associations are interchangeably used herein.

In some embodiments, the member may be made aware of more efficient use the drug benefit program through a mobile electronic device. For example, the member may be made aware that a particular pharmacy is not in one pharmacy network but that a nearby pharmacy is in the pharmacy network. The notification provided through the mobile device can use the location of the mobile electronic device, and hence the member, to determine an appropriate notification. As a result, timely and/or targeted notifications can be provided that can benefit the member without being overbearing on the member. Examples of the notifications may include a location of a participating pharmacy, the need for the member to inquire regarding refill of a prescription, the need for the member to visit a pharmacy for a refill, a location of a pharmacy along a travel route, a list of pharmacies within a distance from the member, and an inquiry as to whether the member would like to enroll a prescription drug into home delivery. Other notifications may include advice of client-saving opportunities, member-saving opportunities, discounts, coupons, convenience, or directed messaging.

Figure 1:
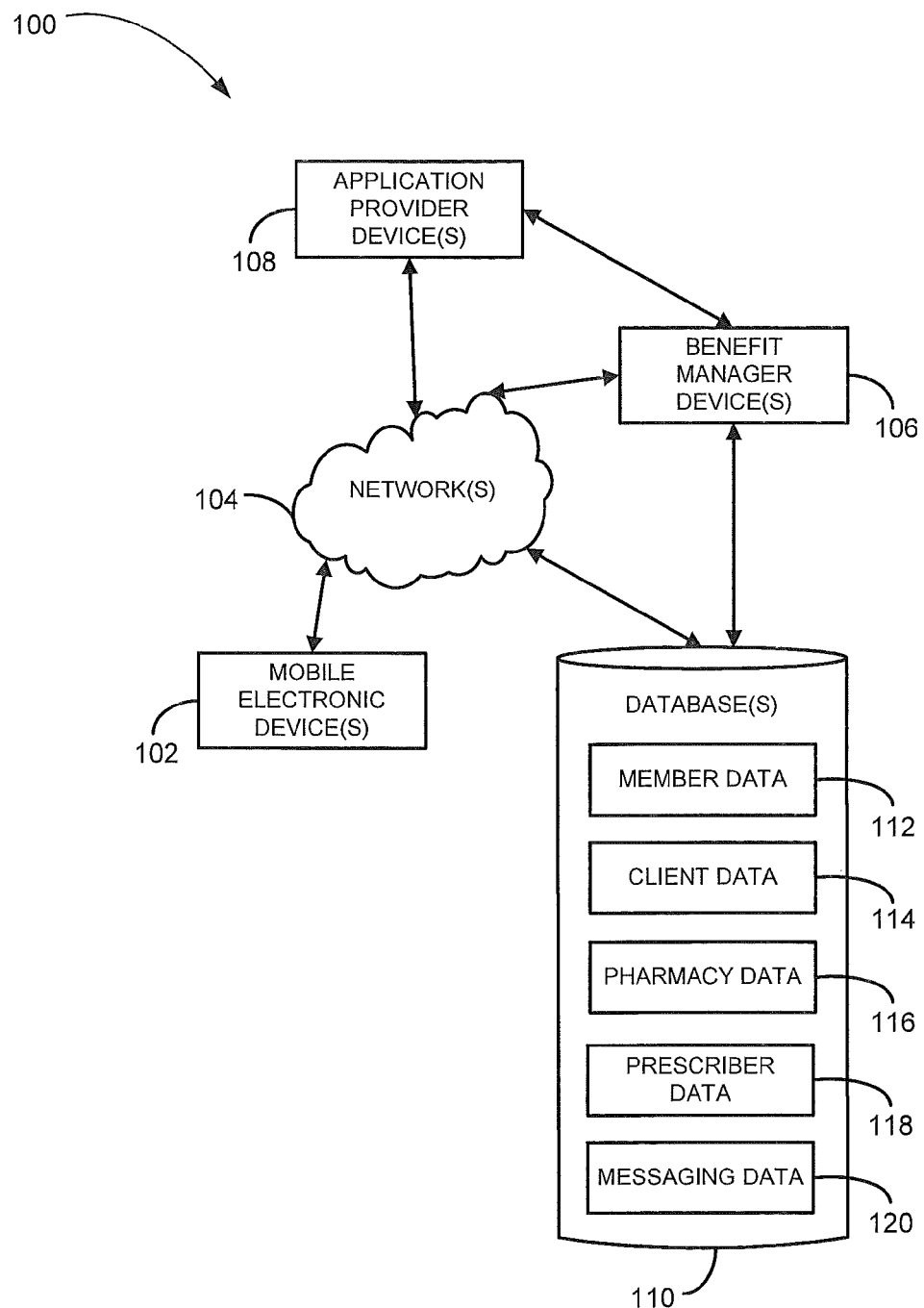
FIG. 1 is a block diagram of an example system, according to an example embodiment.

FIG. 1 is a block diagram of an example system 100, according to an example embodiment. The system 100 is an example environment in which a member, or a device operator assisting the member, may be notified based on the location of the member or device operator acting on behalf of the member. The system 100 includes a mobile electronic device 102 in communication with a benefit manager device 106 over a network 104.

The mobile electronic device 102 is used by a device operator. The device operator may be a member that is either a participant in a drug benefit plan or a beneficiary of the participant (e.g., a spouse or a child of the beneficiary). However, the device operator may be another person acting on behalf of the member. Examples of such people include parents, guardians, and caregivers.

The mobile electronic device 102 may be a stand-alone device that solely provides at least some of the functionality to enable mobile awareness, or may be a multi-use device that has functionality outside of mobile awareness functionality as described herein. Examples of the mobile electronic device 102 include an IPHONE device by Apple, Inc., mobile electronic devices powered by ANDROID by Google, Inc., and a BLACKBERRY device by Research In Motion Limited. These devices may be capable of receiving instructions, storing instructions, executing instructions, storing the execution results or sending information to a further computing device. Other types of mobile electronic devices may also be used.

These can include, but are not limited to, portable computing devices and portable communication devices.

The network 104 by which the mobile electronic device 102 communicates with the benefit manager device 106 may include, by way of example, Mobile Communications (GSM) network, a code division multiple access (CDMA) network, 3rd Generation Partnership Project (3GPP), an Internet Protocol (IP) network, a Wireless Application Protocol (WAP) network, a WiFi network, or an IEEE 802.11 standards network, as well as various combinations thereof. Network 104 may also include optical communications. Other conventional and/or later developed wired and wireless networks may also be used.

The benefit manager device 106 is a device operated by an entity at least partially responsible for creation and/or management of the pharmacy benefit. While the benefit manager operating the benefit manager device 106 is typically a PBM, other entities may operate the benefit manager device 106 either on behalf of themselves, the PBM, or another entity.

Some of the operations of the PBM that operates the benefit manager device 106 may include the following. A member (or a person on behalf of the member) attempts to obtain a prescription drug at a retail pharmacy location where the member can obtain drugs in a physical store from a pharmacist or pharmacist technician, or in some instances through mail order drug delivery from a mail order pharmacy location.

The member may have a co-pay for the prescription drug that reflects an amount of money that the member is responsible to pay the pharmacy for the prescription drug. The money paid by the member to the pharmacy may come from the personal funds of the member, a health savings account (HSA) of the member or the member's family, a health reimbursement arrangement (HRA) of the member or the member's family, a flexible spending accounts (FSA) of the member or the member's family, or the like. An employer of the member may directly or indirectly fund or reimburse the member or an account of the member for the co-pay.

The amount of the co-pay paid by the member may vary by the benefit plan of the client with the PBM. The member's co-pay may be based on be a flat co-pay (e.g., $10), co-insurance (e.g., 10%), and/or a deductible (e.g., for first $500 of annual prescription drug spend) for certain prescription drugs, certain types of prescription drugs, and/or all prescription drugs.

In certain instances, the member may not pay the co-pay or may only pay for a portion of a co-pay for a prescription drug. For example, if the usual and customary cost for a generic version of a prescription drug is $4, and the member's flat co-pay is $20 for the prescription drug, the member may only pay $4 to receive the prescription drug. In another example involving a worker's compensation claim, no co-pay may be due by the member for the prescription drug.

In conjunction with receiving the co-pay (if any) from the member and dispensing the prescription drug to the member, the pharmacy submits a claim to the PBM for the prescription drug. The PBM may perform certain adjudication functions including verifying the eligibility of the member, reviewing the formulary to determine appropriate co-pay, coinsurance, and deductible for the prescription drug, and performing a drug utilization review (DUR) on the member. The PBM then adjudicates the claim associated with the prescription drug and provides a response to the pharmacy following performance of the aforementioned functions. As part of the adjudication, the client (or the PBM on behalf of the client) ultimately reimburses the pharmacy for filling the prescription drug when the prescription drug was successfully adjudicated. The aforementioned adjudication functions generally occur before the co-pay is received and the prescription drug dispensed. However, the operations may occur simultaneously, substantially simultaneously, or in a different order. In addition, more or less adjudication functions may be performed as part of the adjudication process.

The amount of reimbursement paid to the pharmacy by the client and/or member may be based at least in part on the type of pharmacy network in which the pharmacy is included. Other factors may be used to determine the reimbursement amount in addition to the type of pharmacy network.

The mobile electronic device 102, operating on its own or in combination with the benefit manager device 106, may generate a notification or otherwise promote mobile awareness at least partially based on the location of the member (e.g., when the member is acting as a device operator or when a device operator is acting on behalf of the member) and/or a device operator acting on behalf of the member. The notification may be provided to the device operator through a display on the mobile electronic device 102, audibly on the mobile electronic device 102, through a different device by transmission from the mobile electronic device 102, or otherwise. Multiple channels may be used to communicate the notification to the device operator and/or non-device operating member.

In some embodiments, a mobile application or app may be downloaded, installed, and launched on the mobile electronic device 102 to enable the promotion of the mobile awareness. The mobile application may take advantage of hardware and/or software functionality provided by manufacturers of the mobile electronic device 102 and/or developers of the operating system of the mobile electronic device 102. For example, the mobile application may use the SAFARI web browser on the IPHONE device, the webkit browser on an ANDROID device, MOBILE INTERNET EXPLORER on a WINDOWS MOBILE device, or mapping functionality on any of the aforementioned devices. The mobile application may include instructions that when executed on the mobile electronic device 102 or in the benefit manager device 106 cause a machine to change its state or perform tasks within the machine and with other machines. The tasks may take information and change the information to a different output.

The mobile application may be downloaded from an application provider device 108 or directly from the benefit manager device 106. In general, the application provider device 108 is an entity that makes available mobile applications created by the application provider and/or third parties (e.g., the benefit manager) for download and use on mobile electronic devices. Examples of companies that operate the application provider device 108 include Apple, Inc. through its operation of ITUNES STORE, Google, Inc. through its operation of ANDROID MARKET, AT&T through its operation of its APPCENTER, and Research In Motion Limited through its operation of BLACKBERRY APP WORLD. Each of these application provider device companies can host and supply proprietary apps, open apps, and apps by third parties. Updated versions of the mobile applications and/or data to be used by the mobile applications may be provided by the benefit manager device 106, the application provider device 108, or may otherwise be provided.

The mobile electronic device 102 may be in a client-server relationship with the benefit manager device 106 and/or the application provider device 108, a peer-to-peer relationship with the benefit manager device 106 and/or the application provider device 108, or in a different type of relationship with the benefit manager device 106 and/or the application provider device 108.

The benefit manager device 106 may be in communication directly (e.g., through local storage) and/or through the network 104 (e.g., in a cloud configuration or software as a service) with a database 110. The database 110 may store member data 112, client data 114, pharmacy data 116, prescriber data 118, and/or messaging data 120.

The member data 112 includes information regarding the members associated with the benefit manager. Examples of the member data 112 include name, address, telephone number, e-mail address, prescription drug history, and the like. The member data 112 may include a client identifier that identifies the client associated with the member and/or a member identifier that identifies the member to the client.

The client data 114 includes information regarding the clients of the benefit manager. Examples of the client data 114 include company name, company address, contact name, contact telephone number, contact e-mail address, and the like.

The pharmacy data 116 includes information regarding pharmacies. The pharmacy data 116 may include, by way of example, location data regarding the location of the pharmacies, information data regarding the pharmacy hours and/or telephone number, pharmacy network association data defining the pharmacy network associations of which the pharmacies are associated, and the like.

The prescriber data 118 includes information regarding prescribers. The pharmacy data 118 may include, by way of example, location data regarding the location of the prescribers, information data regarding the prescriber hours and/or telephone number, prescriber network association data defining the prescriber network associations of which the prescribers are associated, and the like. The prescribers may be at a physician's office, a hospital, a location associated with a PBM, or the like.

The messaging data 120 includes data used to send notifications to members. For example, the messaging data may reflect standardized messages used for all members, specific messages for specific members, and the like.

Certain data from the database 110 may be stored on the mobile electronic device 102 separate from or in addition to the data stored in the database 110. In some embodiments, the data may be stored on the mobile electronic device 102 instead of in the database 110. In some embodiments, the mobile electronic device 102 is pre-loaded with certain data. For example, select pharmacy information may be pre-loaded on the mobile electronic device 102 based on past adjudication information, a preferred or unpreferred pharmacy, past travel paths of the member, past pharmacies that have filled the prescription drug, inquiry of drug availability with preferred pharmacies, price comparison with other pharmacies, or the like.

While the system 100 in FIG. 1 is shown to include single devices 102, 106, 108, multiple devices may be used. The devices 102, 106, 108 may be the same type of device or may be different device types. When multiple devices are present, the multiple devices may be of the same device type or may be a different device type. Moreover, system 100 shows a single network 104; however, multiple networks can be used. The multiple networks may communicate in series with each other to link the devices 102, 106, 108 or in parallel to link the devices 102, 106, 108.

In some embodiments, at least some of the functionality of the application provider device 108 may be included in the benefit manager device 106. In such embodiments, the application may be downloadable directly from the benefit manager device 106 or at direction of the benefit manager device 106 from the database 110, which may store the application.

Figure 2:
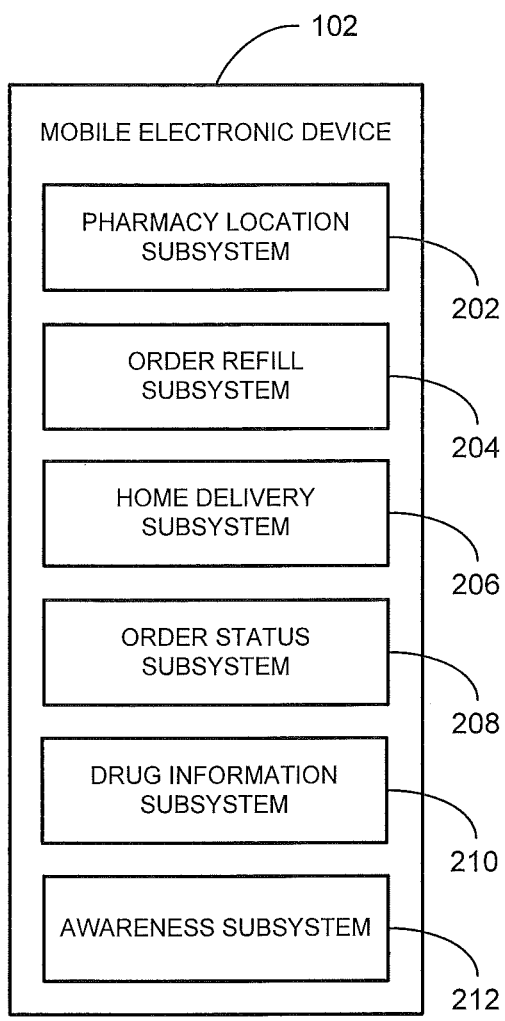
FIG. 2 is a block diagram of an example mobile electronic device that may be deployed within the system of FIG. 1, according to an example embodiment.

FIG. 2 illustrates the mobile electronic device 102, according to an example embodiment. The mobile electronic device 102 may be used by the device operator to generate notifications that promote mobile awareness. The mobile electronic device 102 may be deployed in the system 100, or may otherwise be used.

The mobile electronic device 102 may include a pharmacy location subsystem 202, an order refill subsystem 204, a home delivery subsystem 206, an order status subsystem 208, a drug information subsystem 210, and/or an awareness subsystem 212.

The pharmacy location subsystem 202 enables the device operator of the mobile electronic device 102 to locate a nearby pharmacy. Examples of nearby pharmacies include the physically or geographically closest pharmacies, pharmacies within a certain distance that have the shortest drive time from the current location of the mobile electronic device 102, a pharmacy with a shortest wait time for prescription fulfillment, or the like.

The order refill subsystem 204 enables the device operator to obtain refills for prescription drugs of the member and/or the member's family. The prescription drugs may have been previously filled at retail, through mail order, or otherwise.

The home delivery subsystem 206 enables the device operator to start home delivery service for prescription drugs. The home delivery service through mail order may be for a single prescription drug or multiple prescriptions drugs of the member and/or the member's family.

The order status subsystem 208 enables the device operator to review the status of orders for prescription drugs. Thus, through the order status subsystem 208, the status of a specific order of a member (e.g., the device operator) and/or the member's family may be reviewed. The status of current orders and/or past orders of the member and/or the member's family may also be available for review.

The drug information subsystem 210 enables the device operator to obtain drug information about prescription drugs. The device operator can interact with the drug information subsystem 210 (e.g., via a user interface) to search by drug name. In addition, the device operator can interact with the drug information subsystem 210 to browse by prescription drug name alphabetically through drug navigation. The provided information on prescription drugs may be information included within the DRUGDIGEST database. This prescription drug data may be stored in the database 110, or may be received through interaction with a different computing device and/or database.

The awareness subsystem 212 promotes mobile awareness to the device operator through notifications.

Figure 3:
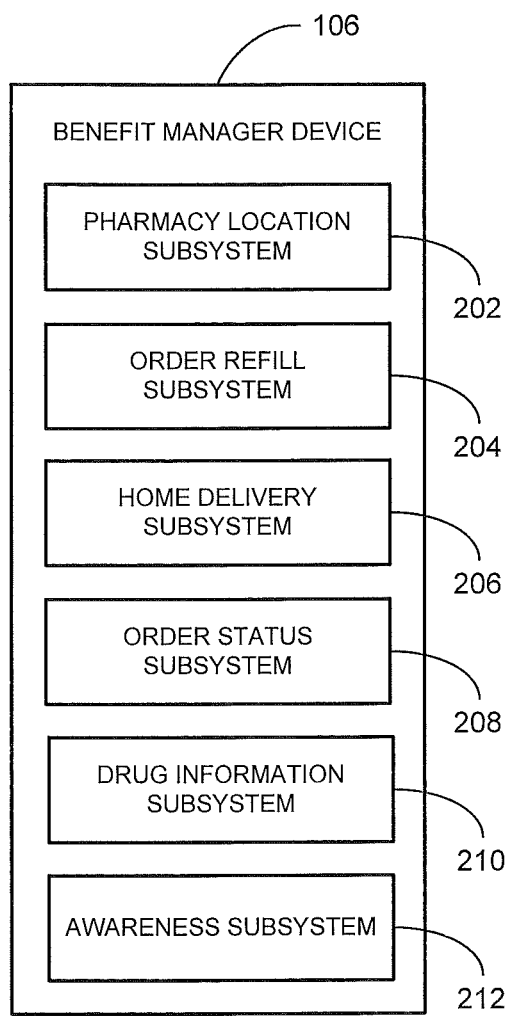
FIG. 3 is a block diagram of an example benefit manager device that may be deployed within the system of FIG. 1, according to an example embodiment.

FIG. 3 illustrates the benefit manager device 106, according to an example embodiment. The benefit manager device 106 may be deployed in the system 100, or may otherwise be used.

The benefit manager device 106 may include the pharmacy location subsystem 202, the order refill subsystem 204, the home delivery subsystem 206, the order status subsystem 208, the drug information subsystem 210 and/or the awareness subsystem 212. In some embodiments, one or more of the various subsystems 202-212 when used may provide server-side functionality to the mobile electronic device 102. By way of example, the awareness subsystem 202 may be deployed in both the mobile electronic device 102 and the benefit manager device 106. The mobile electronic device 102 may then perform some of the functionality while other functionality is performed by the benefit manager device 106.

Figure 4:
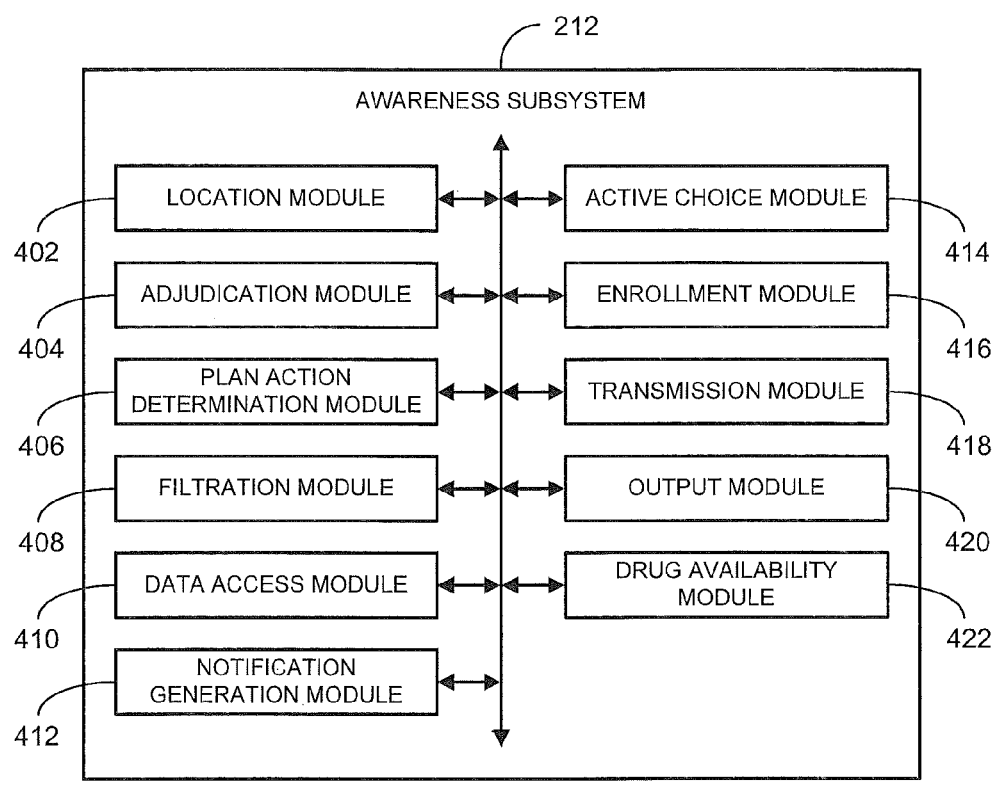
FIG. 4 is a block diagram of an example awareness subsystem that may be deployed within the mobile electronic device of FIG. 2 or the benefit manager device of FIG. 3, according to an example embodiment.

FIG. 4 illustrates an example awareness subsystem 212 that may be deployed in the mobile electronic device 102, the benefit manager device 106, or otherwise deployed in another system. One or more modules are communicatively coupled and included in the awareness subsystem 212 to enable promotion of mobile awareness. The modules of the awareness subsystem 212 that may be included are a location module 402, an adjudication module 404, a plan action determination module 406, a filtration module 408, a data access module 410, a notification generation module 412, an active choice module 414, an enrollment module 416, a transmission module 418, a output module 420, and/or a drug availability module 422. Other modules may also be included.

In some embodiments, the modules of the awareness subsystem 212 may be distributed so that some of the modules are deployed in the mobile electronic device 102 and some modules are deployed in the benefit manager device 106. In one embodiment, the modules are deployed in memory and executed by a processor coupled to the memory. The functionality contained within the modules 402-422 may be combined into a lesser number of modules, further divided among a greater number of modules, or redistributed among existing modules. Other configurations including the functionality of the modules 402-422 may be used.

The location associated with the member is accessed or obtained by the location module 402. The location as accessed may be of the mobile electronic device 102, where the member is located or perceived to be located, where a non-member device operator is located or perceived to be located, or otherwise. The location may be identified in terms of street address, latitude and longitude coordinates, a different type of geographic location identifier or physical location identifier, or otherwise.

The location may be accessed by the location module 402 periodically, on member request, upon application launch, or otherwise. The location module 402 may access the location in real-time or at a delay. The accessed location may also be a perceived location associated with the member based on or using a travel route with the device operator that is operating the mobile electronic device 102.

In some embodiments, the location associated with the mobile electronic device 102 may reflect the current location of the member, regardless of whether the member is in possession of the mobile electronic device 102 or whether a device operator is operating the mobile electronic device 102 on behalf of the member. The location may also be a typical location for the member, e.g., home, business, club, workout facility, or the like.

The location may be a retail pharmacy or within proximity of a retail pharmacy (e.g., 20 feet, 50 feet, 100 feet, 1000 feet, etc.). The retail pharmacy may be, for example, a stand-alone retail pharmacy, a pharmacy within a different service provider (e.g., a grocery store or a retail product store), be located within a hospital or other care unit.

The location may be associated with a prescriber (e.g., a doctor/physician or an office of a doctor/physician). The location may be associated with a different type of health care service provider (e.g., a dentist, an ophthalmologist, a chiropractor, etc.).

The location may be accessed by receiving identification of the location associated with the member. For example, the benefit manager device 106, the application provider device 108, or another device may transmit an actual or perceived location of the device operator (e.g., a member or non-member device operator that is operating the mobile electronic device 102).

In some embodiments, the location module 402 determines the location associated with the member. The location module 402 may include or communicate with a Global Positioning System (GPS) receiver, an accelerometer, and/or other types of software and/or hardware to determine location of the mobile electronic device 102.

The location module 402 may include a position navigation system or functionality of a position navigation system. Examples of navigation systems include a GPS system, a BeiDou navigation system, a COMPASS system, a Galileo system, a GLONASS system, an Indian Regional Navigational Satellite System (IRNSS), a QZSS system, and the like. Moreover, these systems can use Real Time Kinematic (RTK) satellite navigation to provide real-time corrections of the positioning signal sent down. The systems can also use differential correction signals in North American from the FAA's WAAS satellites. The location module 402 may use wireless signals such as Wi-Fi to determine the location of the mobile electronic device 102.

In some embodiments, the location may be accessed by the location module 402 via an authorization or eligibility request received from a pharmacy. For example, if the member should present a health savings account or insurance card during a purchase or attempted purchase, the pharmacy may transmit an authorization request to the benefit manager device 106. The benefit manager device 106 may identify the location of the pharmacy and transmit information to the mobile electronic device 102 that indicates or may be used to determine the current location of the device operator that is operating the mobile electronic device 102.

The location may also be based upon a hierarchical process wherein a real-time location is first selected. If a real-time location is not available, then the last known location of the device operator may be selected. Finally, if a real-time or recent location of the device operator cannot be determined, the location module 402 may select a home location of the member.

In some embodiments, the adjudication module 404 is deployed in the awareness subsystem 212 to adjudicate a prescription drug claim associated with the member. The location module 402 may then determine the location associated with the member based on adjudication of the prescription drug claim.

In general, the location module 402, the methods, and the other systems described herein are generally described as though the device operator is the member. If the device operator is not the member, the location module 402, the methods, and the other systems may use the location associated with the member even though the member is not at or within the same general location as the device operator, may use the location associated with the device operator irrespective of the location associated with the member, may use the location associated with the device operator and the location associated with member, or may otherwise handle the location difference of the member and the device operator. Thus, use of the terms device operator and member should not interpreted restrictively with the methods and systems described herein.

The plan action determination module 406 determines a drug benefit plan action based on the location associated with the member. In general, the drug benefit plan action is a determination of certain information or a type of information that is associated with the prescription drug benefit on which the benefit manager wants the device operator to be aware. Such desire can be solely based on the benefit manager or with the input of others such as the client, the pharmacy network, or the like. In some embodiments, the drug benefit plan action is an action that is at least partially at the direction of a pharmacy benefit manager that administers the drug benefit plan. In some embodiments, the determination of the drug benefit plan action and/or the drug benefit plan action is triggered based on the location associated with the member.

The plan action determination module 406 is not limited to determining a drug benefit plan action based solely on the location associated with the member. For example, in some embodiments the plan action determination module 406 may access the member data 112 associated with the member and/or the client data 114 associated with the client of the member. The accessed data may then be used by the plan action determination module 406 to determine the drug benefit plan action. For example, the accessed data may include the name of the member, an identifier of the prescription drug plan covering the member, a name and location of a prescriber that has prescribed a drug, a drug identifier, a name and a location of a pharmacy that filled a prescription drug, or the like. A single field or multiple fields of data may be accessed. Thus, in some embodiments, the drug benefit plan action may be member and/or client specific.

In some embodiments, the accessed data may be downloaded from the benefit manager device 106 to the mobile electronic device 102 prior to the determination performed by the plan action determination module 406. For example, pharmacy location data that includes an additional pharmacy different from the pharmacy the member currently uses may be downloaded to the mobile electronic device. The additional pharmacy may be a pharmacy within a certain travel time from the location associated with the mobile electronic device 102, within a certain distance or a set number of pharmacies, or otherwise be a different pharmacy.

The plan action determination module 406, in some embodiments, may use predetermined data (e.g., on the mobile electronic device 102) to narrow down a number of locations for possible identification as being associated with the member/device operator to a more reasonable set of locations. As generally described below, certain data may be filtered to create filtered data that reduces the number of locations. For example, filtered data may be used so that instead of comparing the location associated with the member/device operator with all possible pharmacy locations within a city or other geographic region, only the pharmacy locations within or outside of a pharmacy network may be used for comparison.

The determination of the drug benefit plan action by the plan action determination module 406 may include analysis of the stored data (e.g., as stored in the database 110, in the mobile device 102, and/or in the benefit manager device 106) to determine a historical trend. The historical trend may then be used to determine the drug benefit plan action.

Logic may be used to select which of multiple drug benefit actions that have been determined is selected. For example, the hierarchical logic may provide a selection order for an action associated a need to refill a prescription drug, a failure of a member to maximize a prescription drug benefit, availability of a generic or similar branded drug, or the like. The logic may be hierarchical based on client and/or benefit manager preferences, hierarchical based on other preferences or factors, non-hierarchical, or otherwise.

In some embodiments, the plan action determination module 406 determines the location associated with the mobile electronic device 102 and compares it with the geographic location of a previously provided medical service (e.g., a refill of a prescription drug). Upon detecting a match between the location associated with the mobile electronic device 102 and the geographic location, a drug benefit plan action may be determined.

In some embodiments, location criterion may be used by the plan action determination module 406 to determine a drug benefit plan action. For example, the plan action determination module 406 may determine whether the location associated with the member satisfies a prescriber location criterion and/or a pharmacy location criterion. A drug benefit plan action may then be selected based on a determination that the location associated with the member satisfies the prescriber location criterion and/or the pharmacy location criterion.

A single location criterion or location criteria may be used by the plan action determination module 406. While prescriber location criterion and pharmacy location criterion are described as examples of location criteria, other types of criteria may also be used. Examples of the prescriber location criterion include that the member is within a distance of a prescriber location or that the member is at a prescriber location. Examples of the pharmacy location criterion include that the member is within a distance of a retail pharmacy location or that member is at a retail pharmacy location.

In some embodiments, the determination of whether the location associated with the member satisfies the prescriber location criterion includes accessing prescriber location data associated with a prescriber and comparing the location associated with the member with the prescriber location data associated with the prescriber to determine whether the prescriber location criterion is satisfied.

The prescriber data may be accessed by receiving member filtered prescriber data. The member filtered prescribed data may be filtered for the member based on past travel data of the member, distance from the location associated with the member, predicted travel of the mobile electronic device 102, prescription drug history data of the member, or the like. The filtered prescriber location data associated with the prescriber may then be used to determine whether the prescriber location criterion is satisfied.

Data may be filtered by the filtration module 408. In some embodiments, the filtration module 408 may access prescription drug history data of the member and filter the prescriber data based on the prescription drug history data of the member to obtain member filtered prescriber data including filtered prescriber location data. The filtered prescriber location data may then be used by the plan action determination module 406.

In some embodiments, the filtration module 408 may filter using the location by distance from the determined location. The distance can be a limited to the specific determined location. In an example embodiment, only plan action benefits that are available without travel to a second location are determined for the member. In an example embodiment, the distance may be based on predicted travel of the device operator/member associated with the mobile electronic device 102. A predicted travel direction may be at least partly based on the determined location.

In some embodiments, the filtration module 408 may access prescription drug history data of the member, filter the pharmacy data 116 based on the prescription drug history data of the member to obtain member filtered pharmacy data. The member filtered prescriber data may include filtered pharmacy location data. The comparison of the location may then include comparing the location associated with the member with the filtered pharmacy location data associated with the prescriber to determine whether the pharmacy location criterion is satisfied.

In some embodiments, the determination of whether the location associated with the member satisfies the pharmacy location criterion includes accessing pharmacy data that includes a pharmacy location data of a retail pharmacy location and comparing the location associated with the member with the pharmacy location data of the retail pharmacy to determine whether the pharmacy location criterion is satisfied.

In some embodiments, the pharmacy data 116 may be accessed by receiving member filtered pharmacy data. The member filtered pharmacy data may then be filtered for the member based on past travel data of the member, distance from the location associated with the member, predicted travel of the mobile electronic device 102, prescription drug history data of the member, or the like. The filtered pharmacy location data associated with the pharmacy location may then be used to determine whether the pharmacy location criterion is satisfied.

In some embodiments, plan action determination module 406 determines a lower cost alternative prescription drug fill is available at an additional location, the additional location being a different location than the location associated with the member. In some embodiments, the member can also select or set the number of potential second or different locations for a benefit.

An additional location may be within a set distance from the location associated with the member, within a set travel time from the location associated with the member, be adjacent to a known travel path of the member, or the like. Adjacent may be with a certain distance, e.g., less than a mile, 10 miles, 20 miles, or less than 50 miles, or travel time, e.g., less than 5 minutes, less than 10 minutes, less than 20 minutes.

In some embodiments, the plan action determination module 406 may analyze data to identify a historical trend or a due date (e.g., for a refill of a prescription drug, for a meeting with doctor, etc.). The data analysis may be used to select from multiple possible or potential drug benefit plan actions. Thus the analysis may, in some embodiments, affect logic of selection of the benefit plan action.

In some embodiments, the determination of the drug benefit action plan by the plan action determination module 406 is based on a past purchase of the prescription drug by the member from an unpreferred pharmacy.

In some embodiment, the data access module 410 accesses the messaging data 120. The messaging data 120 may be accessed based on the drug benefit plan action, based on the location associated with the member, or the like. Messaging may be preloaded based on past claims data or messaging can be provided in real-time. Messaging can include cost savings, coupons, other, locations, identification as a preferred pharmacy location, etc. In some embodiments, the messaging data 120 as accessed by the data access module 410 may include text, visual, graphical, audio or a trigger signal that could cause a display to show any of the types of message data, which can be stored in the mobile electronic device 102, in the benefit manager device 106, and/or in the database 110.

In some embodiments, the data access module 410 accesses pharmacy data 116. The pharmacy data 116 may include the details of the service provided at the location of a healthcare service provider. For example, the details may include an identifier of a drug provide by a pharmacy or prescribed by a physician.

The notification generation module 412 generates a drug benefit notification based on the drug benefit plan action. The drug benefit notification is used to provide or provides notification to the member. The content of the drug benefit notification is associated with the drug benefit plan in that the benefit manager is at least partially responsible for the drug benefit notification. As such, the drug benefit notification generally relates to a prescription drug, the member's participation in the prescription drug benefit plan, or the like. The drug benefit notification may be customized for the member or may be a non-customized notification. In some embodiments, the customization may be based on the member data 112, the client data 114, and/or the messaging data 120. In some embodiments, generation of the drug benefit notification is based on the drug benefit plan action and the messaging data 120.

The drug benefit notification may include text, an image, a video, and/or a single vibration or a series of vibrations. The drug benefit notification can be in any form that is supportable by the mobile electronic device 102. The drug benefit notification may be presented by the output module 420 through a graphic display, an audio signal (e.g., through a piezoelectric speaker of the mobile electronic device 102), a physical signal (e.g., vibration, which may have a specific pattern) or via a combined graphical and audio presentation. The drug benefit notification may be in the form of a text message, an instant message, e-mail, recorded or streamed audio, recorded or streamed video, or the like. A single drug benefit notification or multiple drug benefit notifications may be generated by the notification generation module 412 based on the drug benefit plan.

The drug benefit notification may include information notifying the member that a lower cost alternative is available at a second location different than the location associated with the member, information notifying the member of an additional location with a pharmacy, the additional location being a different location than the location associated with the member, information notifying the member that a member notification that a lower cost alternative is available at an additional location different than the location associated the mobile electronic device, information notifying the member that the member's prescription drug plan or an aspect of the prescription drug plan has changed or will change, or the like. In some embodiments, the drug benefit drug benefit notification includes a lower cost alternative drug fill indication. In some embodiments, the drug benefit notification includes information notifying that an active decision regarding mail order delivery or retail pickup of a prescription drug is needed.

In some embodiments, the member may be directed by the notifications to ask for generic prescriptions or other medically equivalent medicines, which are typically at a lower cost. The notification regarding generic equivalents may be based upon the general availability of equivalents at lower costs or on the possibility of lower cost alternatives. In some embodiments, the notification to ask for generics may be based on location of the mobile electronic device 102. In some embodiments, the mobile electronic device 102 is at a doctor's office or at a pharmacy that has the generic drugs. The member may be directed through the notification to client savings, member savings, coupons, directed messaging, etc. through the mobile electronic device 102.

The drug benefit notification may include information reminding the member to ask a care provider for a prescribed drug refill when the member is located at or near an associated physician office.

The drug benefit notification may include information notifying the member of a more convenient location for the benefit based on location of the member or the historical travel of the member. In an example embodiment, the drug benefit notification may include a reminder to request a refill of a drug when the location is near a prescriber, e.g., doctor office, clinic, hospital, dentist office, pharmacy, etc. The drug benefit notification may include enrollment in a home delivery service/system for the member's prescribed drug. If the mobile electronic device 102 or the member is determined to be at a pharmacy and a refill prescription is needed, the drug benefit notification may include a request that the member or the pharmacist contact the doctor to authorize the refill prescription.

The drug benefit notification may include notifying the member of the location of a preferred pharmacy, e.g., one that provides an advantage over an unpreferred pharmacy. The drug benefit notification may include a set number of the closest preferred pharmacies. The closest preferred pharmacies can be measured in physical distance or in travel time. The distance may also be measured in proximity to usual travel routes of the member. In some embodiments, drug benefit notification may include notifying a member of preferred pharmacies that are within a select geofence around a location of the member. In general, a geofence is a virtual geographic area defined from a set point in the real world. The area in the geofence can be based on a radius to define a circumference, a polygon, or defined by travel boundaries, e.g., road ways, major roadways, etc. In some embodiments, the geofence can be a set distance from the current location of the member. The set distance can be one mile, 5 miles, 10 miles or any multiple in between or otherwise. The set distances can be determined by the number of likely candidate medical service providers (e.g., pharmacies that will lie within the geofence). In some embodiments, a geofence is set at a distance and then adjusted to have a minimum number of medical service providers in the geofence (e.g., at least one, at least 10, at least 20, or less than 100). This minimum number can be determined in the mobile device 102 or in the benefit manager device 108. The member may also change this number in settings on the mobile device 102 or when enrolling in the PBM plan.

Additional examples of drug benefit notification include the following:
  The drug benefit notification may include information requesting confirmation from the member that the member wishes to acquire a prescription drug from a pharmacy that does not provide a benefit or does not provide maximum benefit.
  The drug benefit notification may include information requesting the member to confirm that the member accepts a higher co-pay amount than at a different pharmacy location.
  The drug benefit notification may include information reminding the member to ask a care provider for a prescribed drug refill when the member is located at or near an associated physician office.
  The drug benefit notification may include information reminding the member to ask a care provider associated with the physician office for a generic equivalent of a prescribed drug.
  The drug benefit notification may include information notifying the member of the location of a preferred pharmacy.
  The drug benefit notification may include information reminding the member to refill a prescription drug.
  The drug benefit notification may include a number of preferred pharmacies that are within a select geofence around a location of the member. In some embodiments, the geofence is a set distance from the current location of the member.

In some embodiments, the identifier of the drug benefit plan may be used to identify a preferred pharmacy network association. The notification generation module 412 may compare the identifier of the pharmacy that filled the drug prescription (the filling pharmacy) with the identifier of preferred pharmacies within the preferred pharmacy network organization. If the identifiers do not match, then the notification generation module 412 may then generate the drug benefit notification. The drug benefit notification may notify the member to obtain a prescription drug from another pharmacy. The drug benefit notification may relate generally to prescription drugs, to a single specific drug that the member is most likely to fill, all prescription drugs of the member, or the like.

When deployed, the active choice module 414 receives an active decision response from the member and transmits an active decision notification. The active decision notification is based on the active decision response. The enrollment module 416 may then receive an enrollment initiation response from the computing device in response to the active decision notification and generates an enrollment display based on, at least in part, the enrollment initiation response.

In some embodiments, the enrollment module 416 may enroll the member in home delivery of prescription drugs. The enrollment may occur in response to receipt of an active choice decision, or may otherwise occur (e.g., at the specific request of the member).

The transmission module 418, when deployed in the awareness subsystem 212, may transmit the drug benefit notification. In some embodiments, the transmission module 418 transmits the drug benefit plan action.

The output module 420, when deployed, generates or renders a display based on generation of the drug benefit notification. The display may include graphics, text, and the like. The drug benefit notification may be, but need not be, included in the display. In some embodiments, the display may include a map with a single location or multiple other locations identified. The locations may include alternate prescriber locations or pharmacy locations beyond the current prescriber location or pharmacy location with which the member (via the mobile electronic device 102) is associated. The display may, instead of or in addition to the location identifiers, may include name, address, and/or other identification associated with prescriber and/or pharmacy locations.

The display as generated or as ultimately presented to the device operator/member may be based on a display criterion. The display criterion may include business logic that defines what or how information is presented on the display, which may be different for different brands and types of mobile electronic devices.

In some embodiments, the drug availability module 422 accesses the prescription drug history data of the member, identifies a current prescription drug associated with the member, and determines whether a generic prescription drug is available for the current a prescription drug. The determination of the drug benefit plan action by the plan action determination module 406 may then be based on the location associated with the member and a determination that the generic prescription drug is available.

Figure 5:
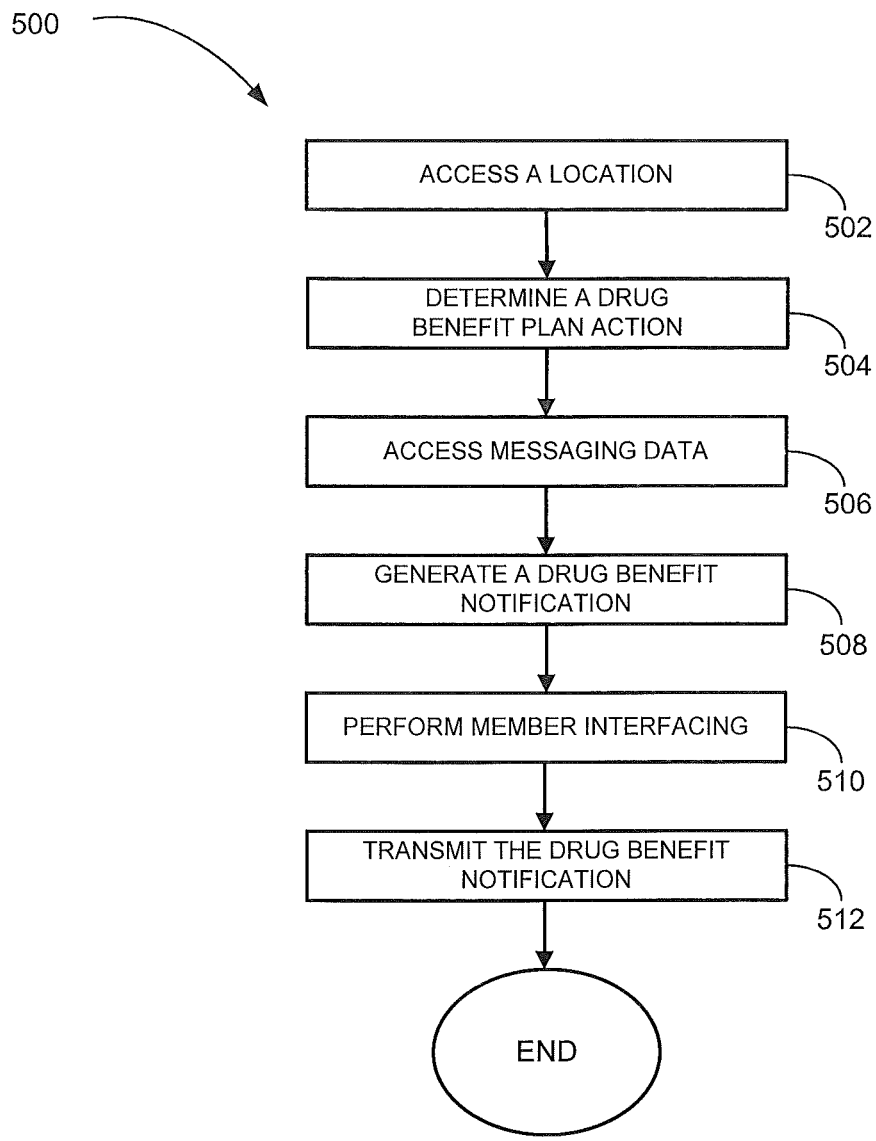
FIGS. 5 and 6 are example process flows illustrating a method for promoting mobile awareness, according to example embodiments.

FIG. 5 illustrates a method 500 for promoting mobile awareness, according to an example embodiment. The method 500 may be performed by the mobile electronic device 102, partially by the mobile electronic device 102 and partially by the benefit manager device 106 and/or the application provider device 108, or may be otherwise performed.

A location associated with a member of a drug benefit plan is accessed at block 502.

A drug benefit plan action is determined at block 504 based on the location associated with the member. The drug benefit plan action is an action at least partially at the direction of a pharmacy benefit manager that administers the drug benefit plan. In some embodiments, determining the drug benefit plan action includes determining a lower cost alternative prescription drug fill is available at an additional location.

The messaging data 120 may be accessed at block 506. The messaging data 120 may be accessed based on the drug benefit plan action and/or the location associated with the member.

A drug benefit notification is generated at block 508 based on the drug benefit plan action. In some embodiments, generation of the drug benefit notification is based on the drug benefit plan action and the messaging data.

Figure 6:
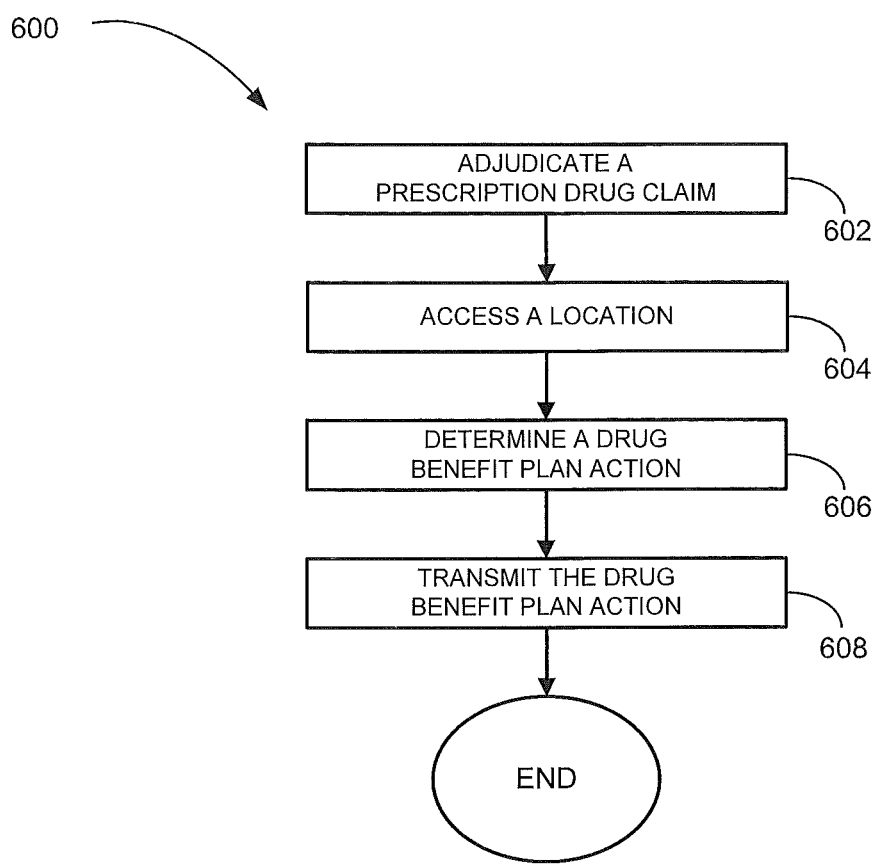

Member interfacing may be performed at block 510. The member interfacing may include rendering a display based on generation of the drug benefit notification. The drug benefit notification may be included in the display and/or the generation of the display may simply use the drug benefit notification as the basis for the display generation. The drug benefit notification may be transmitted at block 512:

FIG. 6 illustrates a method 600 for promoting mobile awareness, according to an example embodiment. The method 600 may be performed by the benefit manager device 106, partially by the benefit manager device 106 and partially by the mobile electronic device 102 and/or the application provider device 108, or may be otherwise performed.

A prescription drug claim associated with the member may be adjudicated at block 602. A location associated with a member of a drug benefit plan is accessed at block 604. In some embodiments, accessing the location includes determining the location associated with the member based on adjudication of the prescription drug claim.

A drug benefit plan action is determined at block 606 based on the location associated with the member.

In some embodiments, the prescription drug history data of the member is accessed, a current prescription drug associated with the member is identified, and a determination whether a generic prescription drug is available for the current a prescription drug is made. The drug benefit plan action may then be determined based on the location associated with the member and a determination that the generic prescription drug is available. The drug benefit plan action is transmitted at block 608.

Figure 7:
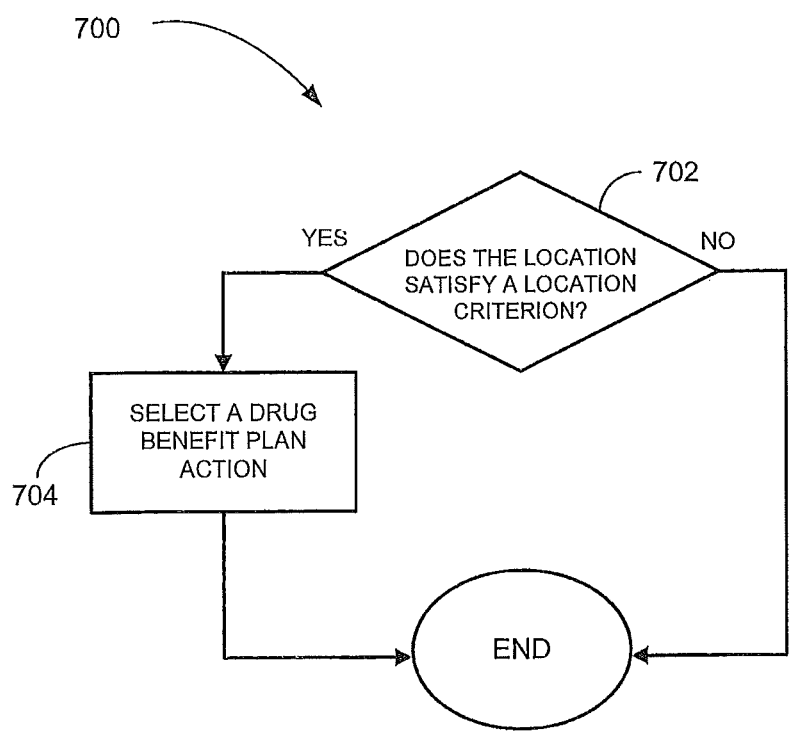
FIG. 7 is an example process flow illustrating a method for determining the drug benefit plan action, according to an example embodiment.

FIG. 7 illustrates a method 700 for determining the drug benefit plan action, according to an example embodiment. The method 700 may be performed at block 504 (see FIG. 5), block 606 (see FIG. 6), or may be otherwise performed.

At decision block 702, a determination is made as to whether the location associated with the member satisfies a location criterion. The location criterion may be a prescriber location criterion, a pharmacy location criterion, or the like. If a determination is made that the member satisfies the criterion, a drug benefit plan action is selected at block 704 based on a determination that the location associated with the member satisfies the location criterion. If a determination is made that the member does not satisfied the criterion at decision block 702, or upon completion of the operations at block 704, the method 700 may terminate.

Figure 8:
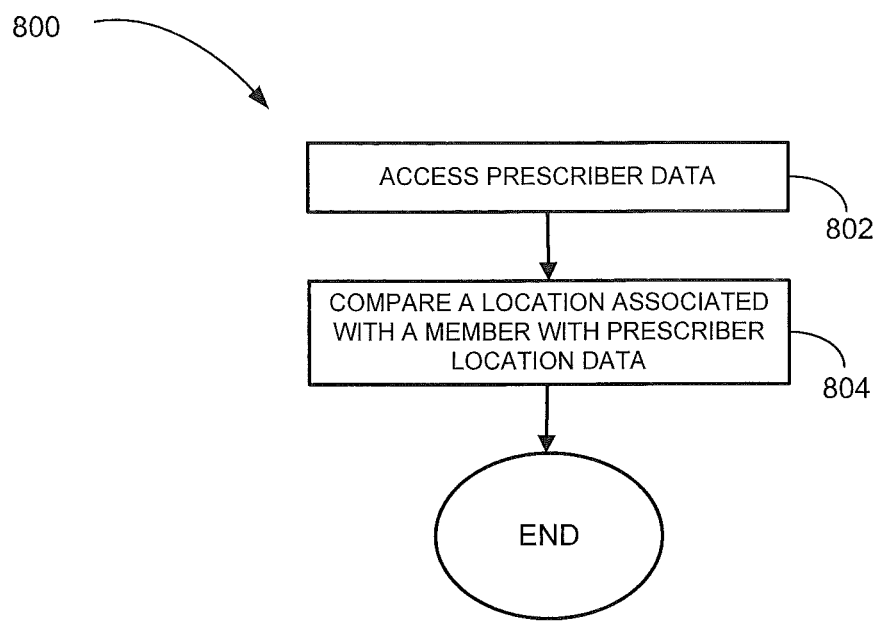
FIG. 8 is an example process flow illustrating a method for determining whether the location associated with the member satisfies the prescriber location criterion, according to an example embodiment.

FIG. 8 illustrates a method 800 for determining whether the location associated with the member satisfies the prescriber location criterion, according to an example embodiment. The method 800 may be performed at decision block 702 (see FIG. 7), or may be otherwise performed.

The prescriber data 118 is accessed at block 802. The prescriber data 118 as accessed includes prescriber location data associated with a prescriber.

In some embodiments, accessing the prescriber data 118 includes receiving member filtered prescriber data. The member filtered prescriber data may be filtered for the member based on past travel data of the member, distance from the location associated with the member, predicted travel of the mobile electronic device, prescription drug history data of the member, or the like. The member filtered prescriber data including filtered prescriber location data.

At block 804, the location associated with the member is compared with the prescriber location data associated with the prescriber to determine whether the prescriber location criterion is satisfied. In some embodiments, comparing the location includes comparing the location associated with the member with the filtered prescriber location data associated with the prescriber to determine whether the prescriber location criterion is satisfied.

Figure 9:
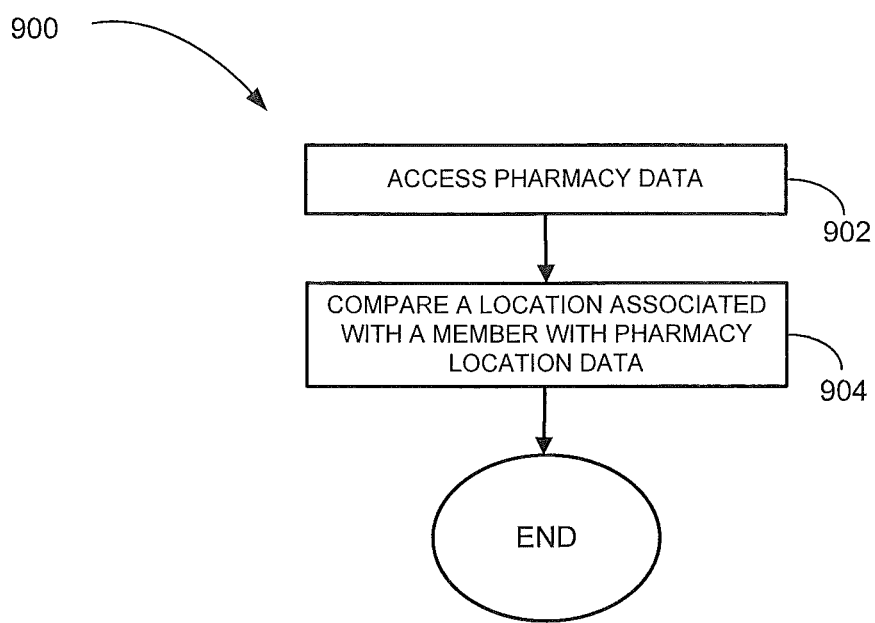
FIG. 9 is an example process flow illustrating a method for determining whether the location associated with the member satisfies the pharmacy location criterion, according to an example embodiment.

FIG. 9 illustrates a method 900 for determining whether the location associated with the member satisfies the pharmacy location criterion, according to an example embodiment. The method 900 may be performed at decision block 702 (see FIG. 7), or may be otherwise performed.

The pharmacy data 116 is accessed at block 902. The pharmacy data 116 as accessed includes a pharmacy location data of a retail pharmacy location.

In some embodiments, accessing the pharmacy data 116 includes receiving member filtered pharmacy data. The member filtered pharmacy data may be filtered for the member based on past travel data of the member, distance from the location associated with the member, predicted travel of the mobile electronic device, prescription drug history data of the member, or the like. The member filtered pharmacy data may include filtered pharmacy location data.

At block 904, the location associated with the member is compared with the pharmacy location data of the retail pharmacy to determine whether the pharmacy location criterion is satisfied. In some embodiments, comparing the location includes comparing the location associated with the member with the filtered pharmacy location data of the retail pharmacy location to determine whether the pharmacy location criterion is satisfied.

Figure 10:
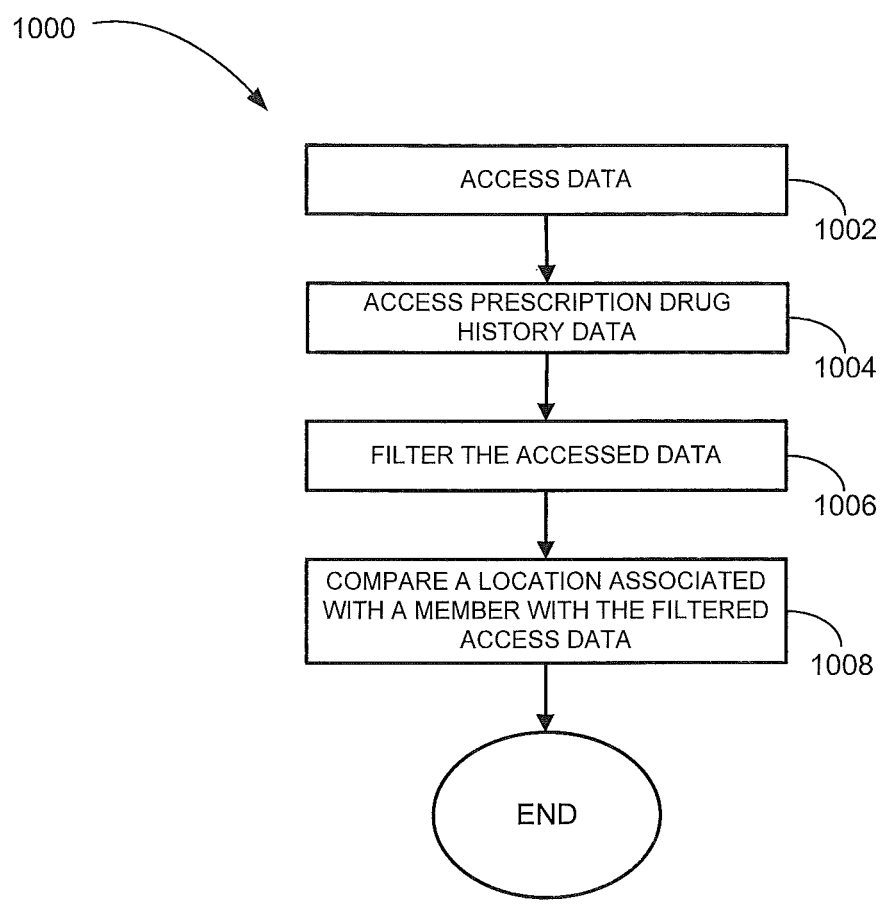
FIG. 10 is an example process flow illustrating a method for determining whether the location associated with the member satisfies a location criterion, according to an example embodiment.

FIG. 10 illustrates a method 1000 for determining whether the location associated with the member satisfies a location criterion, according to an example embodiment. The method 1000 may be performed at decision block 702 (see FIG. 7), or may be otherwise performed.

The accessed data is accessed at block 1002. In some embodiments, the accessed data includes the prescriber data 118 includes prescriber location data associated with a prescriber.

Prescription drug history data of the member is accessed at block 1004.

At block 1006, the accessed data is filtered based on the prescription drug history data of the member to obtain member filtered accessed data. The member filtered accessed data includes filtered location data.

At block 1008, the location associated with the member is compared with the filtered location data to determine whether the location criterion is satisfied.

Figure 11:
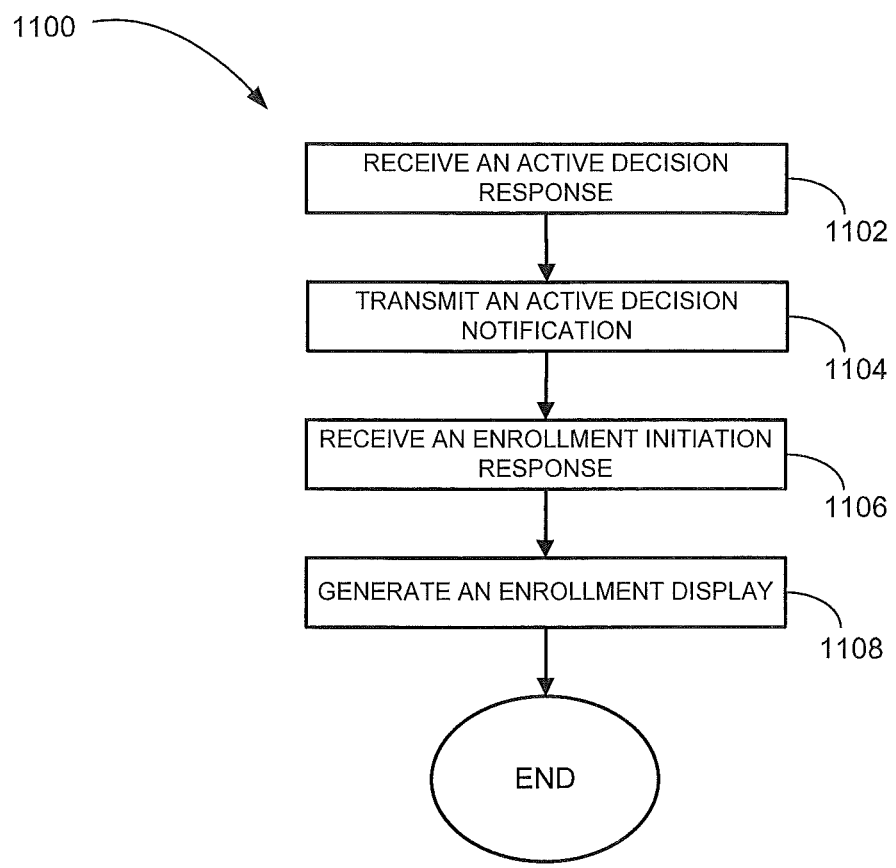
FIG. 11 is an example process flow illustrating a method for performing member interfacing, according to an example embodiment.

FIG. 11 illustrates a method 1100 for performing member interfacing, according to an example embodiment. The method 1100 may be performed at decision block 510 (see FIG. 5), or may be otherwise performed.

An active decision response is received from the member at block 1102.

An active decision notification is transmitted at block 1104.

At block 1106, an enrollment initiation response may be received in response to the active decision notification.

An enrollment display may be generated at block 1108 based on the enrollment initiation response.

Figure 12:
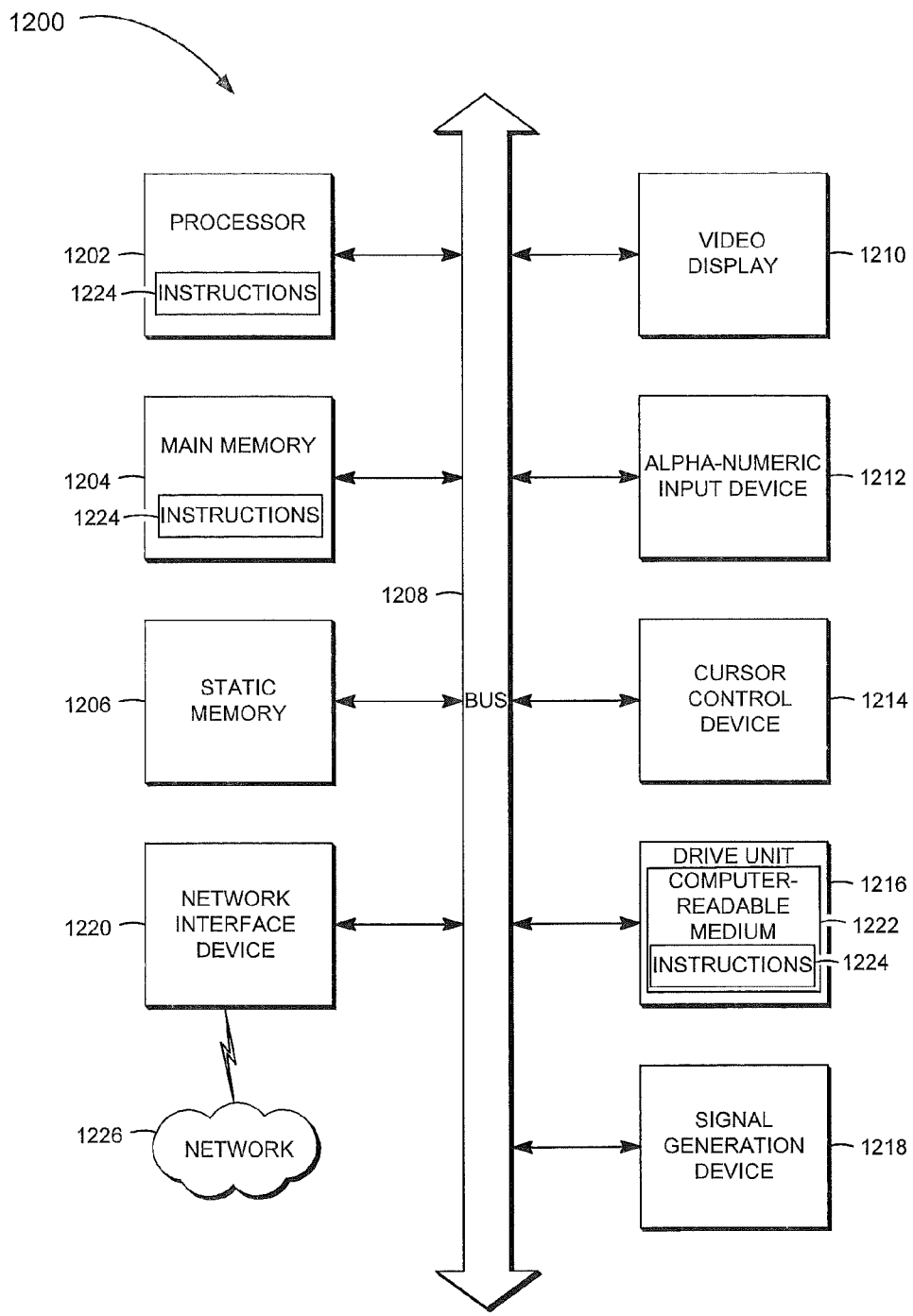
FIG. 12 is a block diagram of a machine in the example form of a computer system within which a set of instructions for causing the machine to perform any one or more of the methodologies discussed herein may be executed or stored.

FIG. 12 shows a block diagram of a machine in the example form of a computer system 1200 within which a set of instructions may be executed causing the machine to perform any one or more of the methods, processes, operations, or methodologies discussed herein. The mobile electronic device 102, the benefit manager device 106, and/or the application provider device 108 may include the functionality of the one or more computer systems 1200.

In an example embodiment, the machine operates as a standalone device or may be connected (e.g., networked) to other machines. In a networked deployment, the machine may operate in the capacity of a server or a client machine in server-client network environment, or as a peer machine in a peer-to-peer (or distributed) network environment. The machine may be a server computer, a client computer, a personal computer (PC), a tablet PC, a gaming device, a set-top box (STB), a Personal Digital Assistant (PDA), a cellular telephone, a web appliance, a network router, switch or bridge, or any machine capable of executing a set of instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein.

The example computer system 1200 includes a processor 1202 (e.g., a central processing unit (CPU) a graphics processing unit (GPU) or both), a main memory 1204 and a static memory 1206, which communicate with each other via a bus 1208. The computer system 1200 further includes a video display unit 1120 (e.g., a liquid crystal display (LCD) or a cathode ray tube (CRT)). The computer system 1200 also includes an alphanumeric input device 1212 (e.g., a keyboard), a cursor control device 1214 (e.g., a mouse), a drive unit 1216, a signal generation device 1218 (e.g., a speaker) and a network interface device 1220.

The drive unit 1216 includes a computer-readable medium 1222 on which is stored one or more sets of instructions (e.g., software 1224) embodying any one or more of the methodologies or functions described herein. The software 1224 may also reside, completely or at least partially, within the main memory 1204 and/or within the processor 1202 during execution thereof by the computer system 1200, the main memory 1204 and the processor 1202 also constituting computer-readable media.

The software 1224 may further be transmitted or received over a network 1226 via the network interface device 1220.

While the computer-readable medium 1222 is shown in an example embodiment to be a single medium, the term "computer-readable medium" should be taken to include a single medium or multiple media (e.g., a centralized or distributed database, and/or associated caches and servers) that store the one or more sets of instructions. The term "computer-readable medium" shall also be taken to include any medium that is capable of storing or encoding a set of instructions for execution by the machine and that cause the machine to perform any one or more of the methodologies of the present invention. The term "computer-readable medium" shall accordingly be taken to include, but not be limited to, solid-state memories, and optical media, and magnetic media. In some embodiments, the computer-readable medium is a non-transitory computer-readable medium.

The term "based on" or using, as used herein, reflects an open-ended term that can reflect others elements beyond those explicitly recited.

Unless clearly and explicitly identified otherwise, the terms "member" and "device operator" are frequently used interchangeably herein.

Certain systems, apparatus, applications or processes are described herein as including a number of modules. A module may be a unit of distinct functionality that may be presented in software, hardware, or combinations thereof. When the functionality of a module is performed in any part through software, the module includes a computer-readable medium. The modules may be regarded as being communicatively coupled.

The inventive subject matter may be represented in a variety of different embodiments of which there are many possible permutations.

In an example embodiment, a location associated with a member of a drug benefit plan is accessed. A drug benefit plan action is determined based on the location associated with the member. The drug benefit plan action is an action at least partially at the direction of a pharmacy benefit manager that administers the drug benefit plan. A drug benefit notification is generated based on the drug benefit plan action. The pharmacy notification benefit is associated with the drug benefit plan.

In an example embodiment, a location associated with a member of a drug benefit plan is accessed. A drug benefit plan action is determined based on the location associated with the member. The drug benefit plan action is an action at least partially at the direction of a pharmacy benefit manager that administers the drug benefit plan. The drug benefit plan action is transmitted.

While the present disclosure in some embodiments refers to prescription drugs and pharmacy benefits, the present disclosure is not so limited. Instead of or in addition to the benefit manager, a health plan may be at least partially associated with the generation of the benefit notification. For example, a method may include accessing a location associated with a mobile electronic device, determining a health care benefit plan action, and generating a health plan benefit notification. Other health care and non-health care organizations may utilize the methods and systems to generate notifications.

Thus, methods and systems for promoting awareness have been described. Although embodiments of the present invention have been described with reference to specific example embodiments, it will be evident that various modifications and changes may be made to these embodiments without departing from the broader spirit and scope of the embodiments of the invention. Accordingly, the specification and drawings are to be regarded in an illustrative rather than a restrictive sense.

The methods described herein do not have to be executed in the order described, or in any particular order. Moreover, various activities described with respect to the methods identified herein can be executed in serial or parallel fashion. Although "End" blocks are shown in the flowcharts, the methods may be performed continuously.

The Abstract of the Disclosure is provided to comply with 37 C.F.R. §1.72(b), requiring an abstract that will allow the reader to quickly ascertain the nature of the technical disclosure. It is submitted with the understanding that it will not be used to interpret or limit the scope or meaning of the claims. In addition, in the foregoing Detailed Description, it can be seen that various features are grouped together in a single embodiment for the purpose of streamlining the disclosure. This method of disclosure is not to be interpreted as reflecting an intention that the claimed embodiments require more features than are expressly recited in each claim. Rather, as the following claims reflect, inventive subject matter may lie in less than all features of a single disclosed embodiment. Thus, the following claims are hereby incorporated into the Detailed Description, with each claim standing on its own as a separate embodiment.

The invention claimed is:

1. A method comprising:
   determining, on a computer processor, a location of a mobile electronic device associated with a member of a drug benefit plan, the location being a current geographic location of the mobile device;
   accessing, on the computer processor, member filtered prescriber data, the member filtered prescriber data includes prescriber location data filtered for the member based on adjudicated claims data of the member, the member filtered prescriber data including filtered prescriber location data of a plurality of member-utilized prescribers from whom the member previously obtained prescriptions as reflected within a plurality of claims of the adjudicated claims data of the member;
   automatically comparing, on the computer processor, the location of the mobile device with the member filtered prescriber location data associated with the prescriber to determine whether a prescriber location criterion is satisfied, the prescriber location criterion including that the mobile electronic device is at least within a range of the prescriber;
   selecting, on the computer processor, a drug benefit plan action based on a determination that the location associated with the member satisfies the prescriber location criterion, the drug benefit plan action being an action for the member to take relative to the prescriber at least partially at the direction of a pharmacy benefit manager that administers the drug benefit plan, the action including a request to move filling of a prescription drug from being performed at retail to being provided through home delivery; and
   generating, on the computer processor, a drug benefit notification based on the drug benefit plan action, the drug benefit being associated with the drug benefit plan.

2. The method of claim 1, wherein the member filtered prescriber data is further filtered.

3. The method of claim 1, wherein accessing the member filtered prescriber data comprises:
   receiving the member filtered prescriber data, the member filtered prescriber data being further filtered for the member based on distance from the location of the mobile electronic device.

4. The method of claim 1, further comprising:
   selecting a plurality of adjudicated claims of the member;
   filtering the prescriber data based on the plurality of adjudicated claims of the member to obtain the member filtered prescriber data,
   wherein automatically comparing the location comprises automatically comparing the location of the mobile electronic device with the filtered prescriber location data associated with the prescriber to determine whether the prescriber location criterion is satisfied.

5. The method of claim 4, further comprising:
   identifying a plurality of prescribers associated with the member based on the plurality of adjudicated claims, wherein filtering the prescriber data is based on identification of the plurality of prescribers associated with the member.

6. The method of claim 1, wherein the prescriber location criterion includes that the mobile electronic device is within a range of a prescriber location.

7. The method of claim 1, wherein the drug benefit notification reflects a lower cost alternative is available at an additional location different than the location associated with the mobile electronic device.

8. The method of claim 1, further comprising:
   transmitting the drug benefit notification.

9. The method of claim 1, further comprising:
   rendering a display based on generation of the drug benefit notification.

10. The method of claim 1, wherein the drug benefit plan action further includes a request to refill the prescription drug currently prescribed to the member.

11. The method of claim 1, wherein the prescriber location criterion includes that the member is at a prescriber location.

12. The method of claim 1, wherein the drug benefit notification includes a reminder to the member to request a prescription drug refill.

13. A non-transitory machine-readable medium comprising instructions, which when executed by one or more processors, cause the one or more processors to perform the following operations:
   determine a location of a mobile device associated with a member of a drug benefit plan, the location being a current geographic location of the mobile device;
   access member filtered prescriber data, the member filtered prescriber data includes prescriber location data filtered for the member based on adjudicated claims data of the member, the member filtered prescriber data including filtered prescriber location data;
   automatically compare the location of the mobile device with the member filtered prescriber location data associated with the prescriber to determine whether a prescriber location criterion is satisfied, the prescriber location criterion including that the mobile electronic device is at least within a range of the prescriber;
   select a drug benefit plan action based on a determination that the location associated with the member satisfies the prescriber location criterion, the drug benefit plan action being an action for the member to take relative to the prescriber at least partially at the direction of a pharmacy benefit manager that administers the drug benefit plan, the action including a request to move filling of a prescription drug from being performed at retail to being provided through home delivery; and
   generate a drug benefit notification based on the drug benefit plan action, the drug benefit being associated with the drug benefit plan.

* * * * *